(12) United States Patent
Buettner-Janz

(10) Patent No.: US 8,016,888 B2
(45) Date of Patent: Sep. 13, 2011

(54) INTERVERTEBRAL DISC PROSTHESIS WITH TRANSVERSALLY ARCHED, CURVED CYCLINDRICAL ARTICULATION SURFACES FOR THE LUMBAR AND CERVICAL SPINE

(76) Inventor: Karin Buettner-Janz, Berlin (DE)

( * ) Notice: Subject to any disclaimer, the term of this patent is extended or adjusted under 35 U.S.C. 154(b) by 330 days.

(21) Appl. No.: 11/379,091

(22) Filed: Apr. 18, 2006

(65) Prior Publication Data

US 2006/0235531 A1 Oct. 19, 2006

Related U.S. Application Data

(63) Continuation-in-part of application No. PCT/DE2005/001886, filed on Oct. 18, 2005.

(30) Foreign Application Priority Data

Oct. 18, 2004 (WO) ............... PCT/DE2004/002333

(51) Int. Cl.
*A61F 2/44* (2006.01)
(52) U.S. Cl. ............... 623/17.14; 623/17.15; 623/17.16
(58) Field of Classification Search .... 623/17.11–17.16; 606/246, 249, 914
See application file for complete search history.

(56) References Cited

U.S. PATENT DOCUMENTS

| 5,258,031 | A |   | 11/1993 | Salib et al. |         |
|-----------|---|---|---------|--------------|---------|
| 5,401,269 | A | * | 3/1995  | Buttner-Janz et al. | 623/17.15 |
| 5,539,409 | A |   | 7/1996  | Mathews et al. |       |
| 5,593,409 | A |   | 1/1997  | Michelson    |         |
| 5,888,226 | A | * | 3/1999  | Rogozinski   | 623/17.16 |
| 6,019,792 | A | * | 2/2000  | Cauthen      | 623/17.14 |
| 6,179,874 | B1 | * | 1/2001 | Cauthen      | 623/17.14 |
| 6,610,093 | B1 | * | 8/2003 | Pisharodi    | 623/17.15 |
| 7,001,433 | B2 | * | 2/2006 | Songer et al. | 623/17.16 |

(Continued)

FOREIGN PATENT DOCUMENTS

CA 2 376 097 12/2000

(Continued)

OTHER PUBLICATIONS

Bomley, Anna, Spinal Devices: Market opportunities and technology trends. Clinica Reports, CBS925, PJB Publications, Ltd., Jun. 2004, Surrey, UK.

(Continued)

*Primary Examiner* — Eduardo C Robert
*Assistant Examiner* — Jan Christopher Merene
(74) *Attorney, Agent, or Firm* — Joyce von Natzmer; Pequignot + Myers LLC

(57) ABSTRACT

An intervertebral disc prosthesis for the total replacement of a intervertebral disc within the lumbar and cervical spine is disclosed. The intervertebral disc prosthesis comprises articulating sliding partners, wherein the upper sliding partner has means for a firm assembly to an upper vertebral body and the lower sliding partner has means for a firm assembly to a lower vertebral body and at least one sliding surface that is between two sliding partners. Functional two- and three part designs are planned and both prostheses have in common, that only a dorsoventral- and rotation movement is possible as a result of laterolaterally aimed, transversally arched, ventrally curved cylindrical convexity(ies) and corresponding concavity(ies), however without an inclination of the sliding partners in a lateral direction. In a further design, the cylindrical articulation surfaces have no curvature, enabling a motion of the sliding partners in only a ventrodorsal direction. According to the invention, the intervertebral disc prostheses are suited for implantation from lateral and ventrolateral, particularly in revision surgeries.

40 Claims, 9 Drawing Sheets

U.S. PATENT DOCUMENTS

| | | | |
|---|---|---|---|
| 7,083,649 B2 * | 8/2006 | Zucherman et al. | 623/17.11 |
| 7,156,876 B2 * | 1/2007 | Moumene et al. | 623/17.13 |
| 7,270,682 B2 * | 9/2007 | Frigg et al. | 623/17.16 |
| 2003/0069586 A1 * | 4/2003 | Errico et al. | 606/99 |
| 2003/0074069 A1 * | 4/2003 | Errico et al. | 623/17.14 |
| 2003/0139813 A1 * | 7/2003 | Messerli et al. | 623/17.11 |
| 2003/0191534 A1 * | 10/2003 | Viart et al. | 623/17.15 |
| 2003/0208273 A1 | 11/2003 | Eisermann et al. | |
| 2004/0024461 A1 * | 2/2004 | Ferree | 623/17.13 |
| 2004/0030390 A1 | 2/2004 | Ferree | |
| 2004/0073310 A1 | 4/2004 | Moumene et al. | |
| 2004/0117021 A1 * | 6/2004 | Biedermann et al. | 623/17.15 |
| 2004/0143332 A1 * | 7/2004 | Krueger et al. | 623/17.14 |
| 2004/0199253 A1 | 10/2004 | Link et al. | |
| 2004/0243240 A1 * | 12/2004 | Beaurain et al. | 623/17.14 |
| 2005/0261772 A1 * | 11/2005 | Filippi et al. | 623/17.13 |
| 2006/0235527 A1 | 10/2006 | Buettner-Janz et al. | |
| 2006/0235528 A1 | 10/2006 | Buettner-Janz | |
| 2006/0241772 A1 | 10/2006 | Buettner-Janz et al. | |

FOREIGN PATENT DOCUMENTS

| | | |
|---|---|---|
| CA | 2376097 A1 | 12/2000 |
| DE | 35 29 761 C2 | 8/1985 |
| DE | 3529761 C2 | 6/1994 |
| DE | 102 42 329 A1 | 4/2004 |
| DE | 10242329 A1 | 4/2004 |
| DE | 203 20 454 U1 | 10/2004 |
| DE | 20320454 U1 | 10/2004 |
| DE | 2004002333 | 7/2005 |
| DE | 2005001886 | 3/2006 |
| EP | 0 560 141 B1 | 2/1993 |
| EP | 0560141 B1 | 10/1996 |
| EP | 1039855 B1 | 10/2000 |
| EP | 1 039 855 B1 | 6/2004 |
| WO | 2004/041131 A2 | 5/2004 |
| WO | WO 2004/041131 | 5/2004 |
| WO | PCT/DE2005/001886 | 4/2006 |

OTHER PUBLICATIONS

Bomley, Anna, Spinal Devices: Market Opportunities and Technology Trends, Clinical Reports, CBS925, PJB Publications, Ltd., Jun. 2004, Surrey, UK.

* cited by examiner

INTERVERTEBRAL DISC PROSTHESIS WITH TRANSVERSALLY ARCHED, CURVED CYCLINDRICAL ARTICULATION SURFACES FOR THE LUMBAR AND CERVICAL SPINE

CROSS REFERENCE SECTION

This is a continuation-in-part application of international application no. PCT/DE2005/001886, filed Oct. 18, 2005 designating the U.S. and claiming priority from international application no. PCT/DE2004/002333, filed Oct. 18, 2004. Both of these applications are incorporated herein in their entirety by reference.

FIELD OF THE INVENTION

The invention relates to an intervertebral disc prosthesis for the total replacement of an intervertebral disc of the lumbar and cervical spine.

BACKGROUND OF THE INVENTION

The idea of function-retaining artificial replacements for intervertebral discs is younger than that for replacements of artificial joints of extremities, but nonetheless about 50 years old [Buttner-Janz, Hochschuler, McAfee (Eds.): The Artificial Disc. Springer Verlag, Berlin, Heidelberg, New York 2003]. It results from biomechanical considerations, unsatisfactory results of fusion surgeries, disorders adjacent to fusion segments and the development of new materials with greater longevity.

The publications and other materials, including patents, used herein to illustrate the invention and, in particular, to provide additional details respecting the practice are incorporated herein by reference.

By means of function-retaining disc implants, it is possible to avoid fusion surgery, i.e. to maintain, or to restore the mobility within the intervertebral disc space. In an in-vitro experiment it is also possible to achieve a normalization of the biomechanical properties of the motion segment to a large extent through the implantation of an artificial intervertebral disc after a nucleotomy.

Implants for the replacement of the whole intervertebral disc differ from those for the replacement of the nucleus pulposus. Accordingly, implants for the total replacement of the intervertebral disc are voluminous; they are implanted via a ventral approach. An implantation of a prosthesis for total replacement of the intervertebral disc immediately after a standard nucleotomy can therefore not be carried out.

The indication for a function-retaining intervertebral disc replacement as an alternative to the surgical fusion includes, besides the painful discopathy, also pre-operated patients with a so-called post discectomy syndrome, patients with a recurrent herniated intervertebral disc within the same segment and patients having a pathology within the neighboring intervertebral disc as a consequence fusion surgery.

Presently, a total of more than 10 different prostheses are clinically used for the total replacement of intervertebral discs. For the lumbar spine the, CHARITÉ Artificial Disc, the PRODISC, the MAVERICK, the FLEXICORE and the MOBIDISC (Overview in Clinical Reports, PJB Publications Ltd., June 2004) are particularly well known, and for the cervical spine the BRYAN prosthesis, the PRESTIGE LP prosthesis, the PRODISC-C and the PCM prosthesis, which will be described below.

The PRODISC prosthesis for the lumbar spine is being implanted since 1999, following its further development to the PRODISC II. The PRODISC prosthesis has been in use as a lumbar spine implant since 1999, until it was replaced by the further developed PRODISC II. Although with respect to its components (a three-part intervertebral disc prosthesis), it is functionally a two-part prosthesis with its sliding partners made of metal and polyethylene. Implantations of the PRODISC are carried out in the lumbar spine and with an adapted model of the prosthesis, the PRODISC-C, also in the cervical spine. Different sizes, heights (achieved by the polyethylene core) and angles of lordosis (achieved by the metal endplates) are available. Bending forward and backward as well as to the right and to the left is possible to the same extent of motion; the axial rotation is not limited in the construction.

The same applies to both two-part prostheses for the cervical spine, the PCM prosthesis with its sliding partners metal and polyethylene and the PRESTIGE LP prosthesis with its sliding partners metal. As special feature of the construction of the PRESTIGE LP prosthesis it has the possibility for an anterior-posterior translation, due to the horizontal ventrally prolonged concavity, which, in a frontal section, has the same radius as the convexity.

The MAVERICK and the FLEXICORE for the lumbar spine are functionally a two-part prostheses with spherical convex-concave sliding partners, both with sliding partners made of metal. In contrast, the MOBIDISC is functionally a three-part prosthesis with sliding partners of metal-polyethylene and two articulation surfaces. One area is a segment of a sphere, as it is in the three afore mentioned prostheses, with a convex and a concave surface of the articulating partners each of the same radius, the other area of the MOBIDISC being plane. Although a limitation of the axial rotation is planned within the plane section, it is not limited within the convex-concave area of articulation. In contrast the FLEXICORE has a small stopping area within the spherical sliding surfaces limiting the rotation movement.

The BRYAN prosthesis is clinically used as a compact prosthesis for total replacement of intervertebral discs of the cervical spine. It is attached to the vertebral bodies by convex titanium plates with a porous surface and achieves its biomechanical properties by virtue of a polyurethane nucleus.

The longest experience exists with the CHARITÉ prosthesis, which is the subject matter of DE 35 29 761 C2 and U.S. Pat. No. 5,401,269. This prosthesis was developed in 1982 by Dr. Schellnack und Dr. Büttner-Janz at the Charité in Berlin and was later on named SB CHARITÉ prosthesis. In 1984 the first surgery took place. The intervertebral disc prosthesis was further developed into model III and has been implanted over 10,000 times worldwide (DE 35 29 761 C2, U.S. Pat. No. 5,401,269) since 1987 and is still being used. The prosthesis is functionally a three-parted being with the sliding partners being metal and polyethylene with two identical spherical sliding surfaces. It has a transversally mobile polyethylene core and the accordingly adapted concave cups within two metal endplates. For the adaptation to the intervertebral space, the CHARITÉ prosthesis provides different sizes of metal plates and different heights of size adapted sliding cores as well as angled prosthetic endplates, which when implanted vice versa in sagittal direction can also be used as replacement for the vertebral body. The primary fixation of the CHARITÉ prosthesis is achieved by six teeth, which are located in groups of three slightly towards the middle next to the frontal and rear edge of each prosthetic plate.

The other prostheses have other primary fixations on their surfaces directed towards the intervertebral bodies, e.g. a sagitally running keel, a structured surface, a convex shape with for instance crosswise running grooves and combinations thereof, also with differently located teeth. Furthermore screw fixations can be used, either from ventral or from within the intervertebral space into the intervertebral body.

To assure a long-term fixation of the prosthetic endplates to the intervertebral bodies and to thus generate a firm connection with the bone, a surface was created in similitude to cement-free hip and knee prostheses, which combines chrome-cobalt, titanium and calcium phosphate in such a way that it is possible for bone to grow directly onto the endplates. This direct connection between prosthesis and bone, without the development of connective tissue, makes a long-term fixation of the artificial intervertebral disc possible and reduces the danger of loosening or displacements of the prosthesis and material breakage.

One primary objective of function retaining intervertebral disc replacements is to closely adapt the motions of the prosthesis to the ones of a healthy intervertebral disc. Directly connected to this is the motion and stress for the facet joints, which following inappropriate biomechanical stress have their own potential for disorders. There can be abrasion of the facet joints (arthritis, spondylarthritis), a formation of osteophytes. As result of these osteophytes and also by a pathologic course of motion of the intervertebral disc alone, the irritation of neural structures is possible.

The healthy intervertebral disc is, in its interactions with other elements of the motion segment, composed in such a way that it allows for limited motion. For example, within the intervertebral disc, motions to the front and back are combined with rotary motions, and side motions are also combined with other motions. The motion amplitudes of a healthy intervertebral disc are very different, with respect to the extension (bending back) and flexion (bending forward) as well as to the lateral bending (right and left) and rotary motion. Although of common basic characteristics, there are differences between the motion amplitudes of the lumbar and cervical spine.

During motion of the intervertebral disc the centre of rotation changes, i.e. the motion of the intervertebral disc does not take place around a fixed center. Due to a simultaneous translation movement of the adjacent vertebrae, the center changes its position constantly (inconstant center of rotation). The prosthesis according to DE 35 29 761 C2 shows a construction which differs relative to other available types of prostheses which are build like a ball and socket joint and as a result move around a defined localized centre of rotation. By virtue of the three-part assembly of the prosthesis according to DE 35 29 761 C2, with two metallic endplates and the interpositioned freely mobile polyethylene sliding core, the course of motion of a healthy intervertebral disc of the human spine is mimicked as far as possible, however without the exact motion amplitudes in the specific motion directions.

A further important feature of the healthy lumbar intervertebral disc is its trapezium shape, which is primarily responsible for the lordosis of the lumbar and cervical spine. The vertebral bodies themselves contribute only to a minor extent to the lordosis. During prosthetic replacement of intervertebral discs the lordosis should be maintained or reconstructed. The Charité disc prosthesis provides four differently angled endplates, which moreover can be combined with each other. However, this surgery requires more surgical effort and has the risk of damaging the vertebral endplates which is associated with a danger of subsidence of the prosthesis into the vertebral bodies. Additionally, if the adjustment of the lordosis is poor and an optimal load of the center of the polyethylene core was not achieved, the prosthesis has to be removed completely.

To avoid sliding or a slip-out of the middle sliding partner from the endplates, DE 35 29 761 C2 discloses a sliding core with a two-sided partly spherical surface (lenticular), with a plane leading edge and at the exterior with a ring bulge, which will lock between the form-adapted endplates during extreme motion. DE 102 42 329 A1 discloses a similar intervertebral disc prosthesis which has a groove around the contact surfaces, in which an elastic ring is embedded that is in contact with the opposite contact area for better guidance.

EP 0 560 141 B1 describes a three-part intervertebral disc prosthesis, which also comprises two endplates and an interpositioned prosthetic core. The intervertebral disc prosthesis, described in this document, provides resistance during rotation of its endplates in opposing directions around a vertical rotary axis without a contact between the prosthetic endplates. This is achieved by a soft limitation of the endplates during rotation onto the prosthesis core caused by the weight, which acts on the plates as a result of the biomechanical load transfer within the spine, because the corresponding radii of curvature differ in a median-sagittal and frontal transection.

The above mentioned models are permanently anchored in the intervertebral spaces as implants. Especially due to a load transfer over too small surface areas, a migration of the endplates into the vertebral bodies and thus a dislocation of the complete implant is possible in middle to long-term use, resulting in artificial stress for the vertebral bodies and the adjacent nerves and in the end for the total motion segment, and leading to new complaints of the patients. The longevity of the polyethylene also needs to be discussed because destructions of the sliding cores has been observed, which necessitated revision surgery, so far in the form of a fusion of the motion segment The risk of postoperatively persisting complaints is higher if the facet joints of the surgical segment already show signs of arthritis at prosthetic implantation. It also has to be taken into account that a too large segmental range of motion, resulting from the design of the prosthesis, may potentially lead to new complaints for the patient. This is most likely caused by an overloading or malapropos stress on the facet joints, which may lead to painful arthritis. The same applies to prosthesis that have been implanted frontally inclined or that have postoperatively developed a malapropos positioning. Furthermore, fusion surgery leads to an increased strain on the neighboring segments with the danger of a later indication for surgery at this level. An intervertebral disc prosthesis with a segmental partial function may thus present a solution to this problem.

EP 1 039 855 B1 discloses a partially cylindrical implant for the intervertebral space. This implant has an elastic core, which is located between two end plates that are assembled to an upper and a lower vertebral body. Motion within the intervertebral space is only possible as far as the elastic core can be compressed.

U.S. Pat. No. 5,539,409 also discloses a partially cylindrical implant for the intervertebral space. Such as implant has a rough surface and, as per the invention, is to be filled with substances that will encourage the fusion of the implant with the bone of the neighboring vertebra. A motion of the affected segment of the spine after implantation is therefore not possible.

Furthermore, intervertebral disc prostheses, from the state of the art known, have one or more cylindrical compressible middle parts. An example can be found in CA 2 376 097 A1, which discloses a prosthesis comprising a cylindrical upper and lower hull, in between which a cylindrical middle part made of an elastic material is positioned.

In the intervertebral disc prostheses with a cylindrical core, known from the state of the art, this is mostly made of an elastic material or is firmly assembled to the neighboring vertebral body. U.S. Pat. No. 5,258,031 discloses a lateral section, partially cylindrical, articulation area of a two-part intervertebral disc prosthesis, which permits a bending to the sides via the lateral edges of the cylindrical marginal convexity, so that the load bearing on the endplates is partially only on the edges and so that an increased wear of these regions of the articulation areas is to be expected. Such a prosthesis can only be implanted by ventral surgery because of the size of the keels and/or the fixation of the prosthesis is by means of screwing.

There is a need for an intervertebral disc prosthesis for the total replacement of the intervertebral disc, which will enable a dorsoventral and a rotational motion of a spinal segment, but does not allow for sideways bending. It will be possible to implant the prosthesis by surgery from ventrolateral and lateral as well.

This need is addressed by the present invention. The invention comprises two different types of an intervertebral disc prosthesis, namely a functionally two-part and a functionally three-part prosthesis.

SUMMARY OF THE INVENTION

The functional two-part prosthesis is characterized by
a) a first sliding partner constructed in such a manner, that the opposite side of the side for the assembly with a vertebral body has a convex curvature (convex articulation area, convexity) and the geometry of the convexity is defined by the fact that it correlates to a segment of a cylinder along its longitudinal axis from right to left lateral with a transversal ventrally directed arched curvation, with the convexity being surrounded dorsally, ventrally and to both lateral sides by a edge, and
b) a second sliding partner constructed in such a manner that the opposite side of the side for the assembly with a vertebral body is built with a concave articulation area (concavity) and the geometry of the concavity is defined by the fact that it has a recess corresponding to the convexity of the first sliding partner, and the concavity is surrounded dorsally, ventrally and to both lateral sides by a edge, and
c) the edges of both sliding partners having an outwardly opening angle (aperture angle) towards each other, with
  a. no inclination of the sliding partners towards each other in a lateral direction being possible, and
  b. the maximally possible motion of the sliding partners in dorsoventral direction being limited by a gap-closure of the edges of the two sliding partners, and
d) the rotation of the sliding partners towards each other is limited by the tolerance between convexity and concavity right and left lateral of the transversally curved cylindrical articulation areas.

The functional three-part prosthesis is characterized by
a) the middle sliding partner having on the upper and lower surfaces a convex curvature (convex articulation area, convexity) and the geometry of the convexities being defined by the fact that they correlate to a segment of a cylinder along its longitudinal axis from right to left lateral with a transversal ventrally directed arched curvation, and
b) upper and lower sliding partner constructed with a concave inner articulation area (concavity) and the geometry of the concavities being defined by a corresponding recess to the articulating convexity of the middle sliding partner and the concavities being surrounded dorsally, ventrally and to both lateral sides by a edge, and
c) the edges of the articulating sliding partners having an outwardly opening angle (aperture angle) towards each other, with
  a. no inclination of the sliding partners towards each other in lateral direction being possible, and
  b. the maximally possible motion of the sliding partners in dorsoventral direction being limited by a gap-closure of the edges of the sliding partners, and
d) the rotation of the sliding partners towards each other is limited by the tolerance between the convexities and concavities right and left lateral of the transversally curved cylindrical articulation areas.

Both prostheses comprise of articulating sliding partners of which each upper sliding partner is firmly assembled to an upper vertebral body and each lower sliding partner is firmly assembled to a lower vertebral body and that the sliding partners form interdigitating articulations areas on their inner surfaces that are directed towards each other. The upper and lower sliding partner of a three-part prosthesis as well as both sliding partners of a two-part prosthesis simultaneously act as endplates, having means for an assembly to an upper or lower vertebral body.

The arched curvature of the cylindrical convexities and the corresponding concavities is only intended to a small degree. By virtue of the ventrally arched curvation of the articulation area of the prosthesis another partial function of the natural intervertebral disc, besides the motion in ventral and dorsal direction, is realized, namely rotation. The facet joints in the human body are approximately located on the sector or circularly parallel to it, which is partially formed by the arched curvation of the articulation areas with a particularly advantageous biomechanical influence on the facet joints during rotation. The rotation of the sliding partners towards each other results in less strain and maintains the boundary between the bone and the implant while preserving the prosthesis material.

As per the invention, it is intended that the ventral and dorsal radii of curvature of the cylindrical convexity and the corresponding concavity run towards each other with a constant distance in the transversal overview, because the ventral and dorsal curvature is derived from two circles with different radii but identical midpoints. As per the invention, it is, however, also intended that the segmental arches do not run towards each other with a constant distance and that they either run towards each other in lateral direction or that they have an increasing distance between them laterally. In the first case, the convexity and corresponding concavity would taper off laterally so that more "play" arises for a combined rotation and inclination motion. In the second case the contact area of the convexity with the concavity would be larger, which would result in an improved durability of the material of the articulation areas.

On the whole the maximally possible motion of the sliding partners of an intervertebral disc prosthesis, as per the invention, is defined
a) during dorsoventral inclination of the sliding partners towards each other via the radius of curvature as well as the height of the convexity and concavity and of the respective edge, which surrounds an articulation area ventrally and dorsally, and
b) the aperture angle between the edges of neighboring sliding partners, with it arising from obliquely and/or horizontally running edges of neighboring sliding partners, which during terminal contact of the sliding partners lead to a gap-closure, and
c) by the rotation of the sliding partners with respect to a fictitious vertical axis, the arched curvation(s) and the extent of the arched curvation(s) of the cylindrical convexity(ies) and corresponding concavity(ies) and the tolerance between the convexity and concavity laterally to the right and left respectively at the end of the cylindrical articulation area.

The two- and three-part prostheses are particularly advantageous in cases of implantations in multiple adjacent intervertebral spaces because of the model-immanent stability. They are also advantageous for intervertebral spaces that are inclined to the left or right and which are to be corrected. Furthermore, the two and three part prostheses can be implanted in patients, where the implantation is to be carried out from a lateral or ventrolateral approach, e.g. via a transpsoas approach. Such an indication would, for instance, be given in patients who have previously had surgery to the spine from a ventral approach, who require a change of prostheses after primary implantation of a prosthesis from a ventral approach, because the scarring of the large blood vessels in the ventral region of the spine presents a considerably increased surgical risk in cases of a ventral re-operation. With a lateral approach the annulus fibrosus can be incised generously on one side, so that an optimal prosthesis—with respect to the area—for the purpose of a load transfer over a large area, can be positioned, without a postoperatively arising frontal segmental inclination, as a result of the one-sided lateral liberation of the intervertebral disc. It is further feasible that patients, who have arthritis of the facet joints without osteophytes, can be treated, because postoperatively bending motions to both lateral sides do not stresses these joints.

Because of the narrow anatomical space, the two-part prosthesis is more suited for the cervical spine. The three-part intervertebral disc prosthesis has the advantage that the transversal sliding of two neighboring vertebrae is minimal, resulting in a very favorable adaptation to the bio-mechanics of the motion segment of the lumbar spine. However, the three-part prosthesis enables the simulation of an inconstant center of rotation.

With respect to the present invention the three body axes are described by the following terms: A "sagittal section" or a view in the "sagittal plane" enables a lateral view, because the section plane runs vertically from the front to the back. The term "front" is synonymous "ventral" and the term "back" to "dorsal", because using these terms, the orientation of the prosthesis within the body is indicated. A "frontal section" or the "frontal plane" is a vertical cross-section from one side to the other. The term "lateral" stands for sidewise. Sagittal and frontal sections are vertical sections as they both run in a vertical plane, but 90 degree displaced from one another. A view in the "transversal plane" or a "transversal section" shows a top-view onto the prosthesis, because it is a horizontal section.

With respect to the description and depiction of the present invention, an articulation area signifies that region of the sliding partners, which comprises the curved convex and concave parts of the surfaces, which come into contact or articulate with each other. Because of this the articulation area is synonymous with the term sliding area.

The term "corresponding," with respect to the articulating sliding surfaces designates not only congruent convex and concave shaped surfaces articulating with each other. Moreover this term also designates articulating surfaces that are not completely congruent. Such "deviations" or tolerances regarding the sliding surfaces of articulating sliding partners can be caused by the chosen materials and shapes. Alternatively, the convexity and the concavity may intentionally be not completely congruent, for instance in order to specifically assign the desired range of motion of the articulating partners.

Besides the advantages resulting from the shape of the arched, curved convex-concave parts of the articulation surfaces, as per the invention, the intervertebral disc prostheses have further advantages. The concavities of upper and lower sliding partner of a two- and three-part intervertebral disc prosthesis are each enclosed by a edge, whereas the convexities of a middle sliding partner of a three-part prosthesis range through the whole upper and lower side i.e. the convexities are without edge, or the convexities are each enclosed by a edge with a similar or different breadth.

An edge, as per the invention, indicates an area located between outer rim of the respective sliding partner and convexity(ies) or concavity(ies). The edges of the respective sliding partners run horizontally and/or obliquely and preferably have a plane surface. It is essential for the design of the surfaces of the edges, that during terminal inclination of the sliding partners towards each other a maximally possible contact between the edges of the sliding partners is guaranteed. Should the edges not have a plane surface, they have to in any case be designed in such a way that when they close towards each other, a maximally possible contact arises between them. The height of the edges at the articulation area and the area of the edge along the ventral or dorsal articulation area is equally or differently designed, however the marginal height may vary in such a way from ventral to dorsal that the motion possibility is purposefully larger to the ventral than to the dorsal direction.

The edges of the convexity(ies) and concavity(ies) always have, without incline of the sliding partners towards each other, an outward opening angle (aperture angle) in every sagittal section plane. During terminal inclination of the sliding partners towards each other anteriorly and posteriorly, it comes to a gap-closure between the edges of the articulation areas. The maximal inclination angles are limited by contact of the transition area between convex and concave articulation areas. Although this contact is limiting for the further motion of the sliding partners towards each other, it is not the only area outside the concave-convex articulation areas, which comes into contact at terminal inclination. The edges of the sliding partners up unto their peripheral rim are designed in such a way, that these also participate in the gap-closure.

By this measure, as per the invention, the load bearing surface area is increased at terminal inclination of the prosthesis, during which an inclination of the prosthesis up until its limitation takes place. The areas in contact are further protected against wear because the pressure is taken up by a plane surface and not by small contact areas, resulting in a more durable prosthesis.

As per the invention, it is further intended that a cylindrical convexity has one-sidedly conically diminishing radii along its longitudinal axis. In such a model, the edge has according adaptations so that the ventrodorsal and rotation motions are still possible. By virtue of this "leaning" cylinder it is possible to make adaptations to maladjustment of the intervertebral space and/or to sustain or balance an existing scoliosis, where it is indicated.

In a preferred version it is intended for the cylindrical convexities and corresponding concavities have a curvation that equals zero.

Regarding the material of the prosthesis, as per the invention, it is intended, that the sliding partners are built as a single piece or at least one sliding partner comprises at least two permanent or firmly, but reversibly attached parts, whereas the convexity(ies) and/or the concavity(ies) are the parts being permanently or firmly, but reversibly assembled to the corresponding sliding partner, or the convexity(ies) and/or concavity(ies) having suitable means for a permanent or firm, but reversible assembly, whereby with each other connected parts comprise the same or different materials or the surfaces of the parts are coated equally or differently. As suitable means for the assembly, adaptations of the shape of the parts to be connected, as per the invention, are intended, such as flat broadenings which are part of the edge or which form the whole edge, or recesses.

As far as an intervertebral disc prosthesis comprises permanent or firmly, but reversibly attached parts, it is intended that the assembly is achieved by a tongue and groove assembly, a track and corresponding recess, a snap mechanism, gluing or screwing.

For a three-part intervertebral disc prosthesis, as per the invention, it is intended, that upper and lower sliding partner comprise the same material or are equally coated and the middle sliding partner is made of a different material or is differently coated. It is further intended that all three sliding partners are made of the same material or have the same coating.

The sliding partners are manufactured from well established materials in implantation techniques; for instance upper and lower sliding partner are made of rust free metal and the middle sliding partner of medicinal polyethylene. Other combinations of materials are also possible. The use of other alloplastic materials, which may also be bio-active, is also intended. The sliding partners have a high gloss polish at their contact areas to minimize abrasion (low-friction principle). Furthermore, a coating of the particular sliding partner with appropriate materials is also planned. Favored materials are: titanium, titanium alloys, titanium carbide, alloys of cobalt and chrome or other appropriate metals, tantalum or appropriate tantalum alloys, suitable ceramic materials as well as suitable plastics or compound materials.

For a three-part prosthesis, as per the invention, it is further intended, that the radii of curvature of the cylindrical convexities of upper and lower side of the middle sliding partner as well as the corresponding concavities of the upper and lower sliding partner are identical or different. At identically as well as differently bent convexities on upper and lower side it is, dependent on the design, furthermore intended, that the maximal height of the convexities of the middle sliding partner on the upper and lower side be different so that the convexities consist in the sagittal view of peripheral segments of a circle, which cannot be put together to form a complete circular arch. Depending on the model, the height of the edge of the middle sliding partner is either reduced by the same amount as the height of the convexity(ies), or the height of the edge remains the same or is different from the change of height of the convexity(ies), with the maximal height of the convexities thus remaining the same or being different on the upper and lower side.

By these measures, as per the invention, the total height of the prosthesis is reduced, because the middle sliding partner is flattened. By this design dimensions of the prosthesis are thus reached, which makes it possible to implant it into physiologically extremely small intervertebral spaces. Additionally, such a design enables the variability of the height of the middle sliding partner and by this the possibility to get a prosthesis adapted to the required height.

For a two- or three-part intervertebral disc prosthesis, as per the invention, a maximal aperture angle if 6°-10° including, for example 6°-7°, 6°-8°, 6°-9°, 7°-8°, 7°-9°, 7°-10°, 8°-9°, 8°-10°, during one-sided gap closure of the sliding partners during extension or flexion is intended. The concrete maximal motions can be constructively adapted for the lumbar and cervical spine, without the need of an "individual prosthesis" for every single intervertebral disc. The dorsal and ventral aperture angles correspond to the natural segmental mobility and are reached by suitable choices of convexities and concavities in connection with the design of the surrounding edges. That way a ventrally larger inclination of the sliding partners towards each other than dorsally is enabled, which correlates to the physiological situation of the lumbar spine. To compensate for the tolerances within the motion segment an additional 30 will be included for every direction of motion.

For a functional two part—as well as for a functional three-part intervertebral disc prosthesis, as per the invention, a transversal ventrally directed arched, cylindrical convexity and concavity of articulating sliding partners enables as well as limits a rotation around a fictitious vertical axis. By virtue of this model, as per the invention, a rotation of the sliding partners towards each other is enabled, which depending on the extent of the arched curvature allows a rotation around a fictitious central vertical axis of up to 3 degrees, including up to about 2 degrees or up to about 1 degree, for the lumbar spine and up to 6 degrees, including up to about 5 degrees, up to about 4 degrees, up to about 3 degrees, up to about 2 degrees or up to about 1 degree, for the cervical spine to each side. To compensate for the tolerances within the motion segment an additional 2 degrees to each side is included.

In a further preferred design of a two- or three-part intervertebral disc prostheses, as per the invention, a shift of up to 4 mm, including up to about 3 mm, up to about 2 mm or up to about 1 mm, away from a midline sagittal section to dorsal of the convexity(ies) and corresponding concavity(ies) is intended.

Particularly, a dorsally displaced center of rotation corresponds above all to the physiological situation between the lumbar spine and the sacral bone and at same time the differences between the possible inclination angles in extension and flexion are achieved.

It is furthermore intended that the edges of the sliding partners end outwardly rectangular, otherwise angular, curved or combined straight, curved and/or angular. In the case of three-part prosthesis it is further intended that the convexities of the middle sliding partner peripherally end symmetrically or asymmetrically, rectangularly otherwise angled, in the shape of a hemisphere, rounded off or flattened to both lateral sides. The articulating concavity has a shape corresponding to the lateral shape of the convexity. The middle sliding partner still remains between the upper and lower sliding partner during terminal inclination thus making possible a very compact and economic (with respect to space) construction of an intervertebral disc prosthesis, as per the invention.

A slip out of the middle sliding partner out of this "compact" design of a three part intervertebral disc prosthesis, as per the invention, is prevented by the heights of the convexities on the upper and lower side and the corresponding concavities starting with the edge around the articulation areas and by the closed gap between the edges of the sliding partners at terminal inclination. The convexities are designed in such a way that they will interdigitate deeply enough into the articulating concavities. A sufficient opening of the whole prosthesis post-operatively, which is a prerequisite for a slip out of the middle sliding partner, is thus not possible.

Furthermore, it is intended as per the invention, that in the case of a middle sliding partner of a three part prosthesis, as an additional safeguard, a stop against a slip-out, slip-away or slip-aside (luxation) out of the prosthesis during a gap-closure of all three sliding partners is provided. This is part of the outer edge of the middle sliding partner or the sliding core. The stop of the middle sliding partner is located next to the periphery of the upper and/or lower sliding partner and is higher at least on the upper or the lower side than the edge of the middle sliding partner.

This stop, as an additional safeguard against a slip-out, slip-away or slip-aside (luxation) out of the prosthesis can, as per the invention, also be designed in such a way that it is part of the edge of the middle sliding partner which is higher on the upper and/or lower side than the edge of the middle sliding partner and is conducted within a groove in the edge of the upper and/or the lower sliding partner with the necessary liberty for the maximal sliding motion of the sliding partners.

As per the invention, a stop is an outwardly directed extension of the edge of a middle sliding partner which, as result of its design, is suited to prevent a slip-out of the middle sliding partner out of the concavities of the upper and lower sliding partner. It is not necessary that the stop encloses the middle sliding partner completely, because this could result in a limitation of the maximal mobility of all sliding partners. Where required, it is arranged in definite distances or opposite of positions of the edge, which represent possible positions for a slip-out of the middle sliding partner. If the stop is higher on the upper and lower side than the edge of the middle sliding partner, it can for instance be shaped like a drawing-pin, sticking with the tip from outside into the edge, so that the head of the drawing-pin juts out over the upper and lower edge of the middle sliding partner and prevents a slip-out of the middle sliding partner during a terminal inclination in direction of the drawing pin by "stopping" its movement via contact to the upper and lower sliding partner.

If a stop, as a safeguard to prevent slip-out, is part of the edge of the sliding partners, the height of the convexity depends only—with regard to the anatomy and the material properties—on the wanted maximal inclination angles, which is also influenced by this (see above).

A stop to secure the middle sliding partner of a three-part prosthesis is advantageously shaped in such a way that it also takes part in the gap-closure during terminal inclination of the sliding partners. Due to this fact the stop functions not only as a safeguard, but additionally it increases the load bearing area during terminal inclination of the sliding partners; the advantages of this have been described above. The possibility for such a design, however, depends crucially on the external shape of the upper and lowers sliding partner and the respective breadth of the edge of the convexity and concavity.

In a further design of a three part intervertebral disc prosthesis it is intended that the height of the edge of the middle sliding partner partly or totally continuously increases beginning from the transition area between the convexity and the edge up unto the peripheral edge area. This is intended without the size of the aperture angle changing as a result of an adaptation to the height of the edge of the upper and lower sliding partner. This "dovetail" shape of the edge of the middle sliding partner increases the safeguard against dislocation.

As per the invention, a shape for the upper and lower sliding partner is intended for three part-prosthesis, in which the peripheral edge areas are complete or partly hook-shaped, perpendicular, otherwise angular, curved or a combination thereof in direction of the other outer sliding partner. In this design, the edge of the middle sliding partner is narrower there, so that the middle sliding partner is partly or completed covered by the feature of one or both outer sliding partners, in order to prevent a slip—out of the middle sliding device. Advantageously, the edge of the middle sliding partner is adapted in such a way to the shape of the edge of the outer sliding partners, that during terminal gap-closure as high as possible an area of the articulating sliding partners comes into contact.

Further, it is intended for an intervertebral disc prosthesis, as per the invention, that the outer circumferences of the upper and lower sliding partner may taper off from dorsal to ventral (lumbar spine) or from ventral to dorsal (cervical spine) in a transversal view. This tapering off of the outer circumferences of the upper and lower sliding partner may laterally be in the form of identical curves and is preferably a segment of a circle. Where necessary, area and shape of the outer circumference of the upper and lower sliding partner can be equal or unequal and thus adapted to the size of the respective vertebral body to which they are assembled.

The tapering off shape of the upper and lower sliding partner generally corresponds to the prosthetic plates usable area of a vertebral body in a transversal view and thus leads to an optimal utilisation of the available area of a vertebral body for the anchoring of the sliding partners, with the objective of a load transfer onto as large as possible a surface area of the load, bearing on the sliding partners Adaptations to the sliding partners, as per the invention, of the intervertebral disc prosthesis are further intended, in which upper and/or lower sliding partner are built in such a way in a frontal and/or sagittal section, that the out- and inside of the upper and/or lower sliding partner are parallel or not parallel to each other. By this measure, as per the invention, an intervertebral disc prosthesis, as per the invention, can be adapted to vertebral body endplates, which are not standing parallel in a frontal view or which, in a sagittal view, should build an optimal lordosis and positioning of the sliding areas.

It is further intended, that in a two- and three part design, as per the invention, the convexity (two-part prosthesis) or the middle sliding partner (three-part prosthesis) is parallel or unparallel with respect to a fictitious horizontal. In the case of an unparallel design, upper- and lower side stand in an angle with respect to a fictitious horizontal with the angle being the same above and below or different with a middle sliding partner. The convexity(ies) and corresponding concavity(ies) in the two- and three-part prosthesis are symmetrical or asymmetrical in their surface design. By virtue of the angular convexity or the angular middle sliding partner, adaptations to asymmetries of the intervertebral space, into which the prosthesis is to be implanted, are also possible.

In a preferred model, the transversal ventrally running arched curvation of the convexities each differ from the middle to lateral side. The concavities of the articulation sliding partners have correspondingly arched curvations. In this case of a ventrally asymmetrically running arched curvation, alternative an interruption of the convexity is centrally intended, with in this case the respectively corresponding concavity being able to have an interruption in form of a bridge.

The different arched curvations offer the advantage that adaptations to the different positions of the facet joints can be made. This enables an optimal integration of the position of the facets of the facet joints within the asymmetrically, ventrally arched convexities during rotation.

For a reliable anchorage of the implants within the intervertebral space, a marginal and/or plane interdigitation of the exterior sides of the upper and lower sliding partner serves for the connection with an upper and lower vertebral body. The exterior sides themselves are flat or convex in shape and it is possible to coat the interdigitation or the vertebra-directed surfaces with or without interdigitation bio-actively or blunt. To minimize the risk of fracturing the vertebral body, a fixation with three ventrally arranged and two dorsally placed anchoring teeth is preferred. As an alternative, laterally continuously arranged rows of teeth from front and back or obliquely running rows of teeth are favoured for the implantation of the prosthesis from lateral and ventrolateral approaches and for an improved guidance of the upper and lower sliding partner during implantation between the vertebral bodies, because the forceps of the surgeon can grip in the middle gap between the rows of teeth or into holes of the upper and lower sliding partner at the level with the teeth.

To facilitate implantation or explantation of the intervertebral disc prosthesis, the upper and/or lower sliding partner are furbished with a provision for instruments in a further design. These provisions preferably comprise holes or moulds, into which the required instrument of the surgeon can grip so that a secure fixation of the respective sliding partner is possible.

Furthermore, as absolute measurements for an intervertebral disc prosthesis, as per the invention, a maximal breadth (frontal view) of 14 to 48 mm, including about 16 mm, about 18 mm, about 20 mm, about 22 mm, about 24 mm, about 26 mm, about 28 mm, about 30 mm, about 32 mm, about 34 mm, about 36 mm, about 38 mm, about 40 mm, about 42 mm, about 44 mm or about 46 mm, a maximal depth (sagittal view) of 11 to 35 mm, including about 13, about 15 mm, about 17 mm, about 19 mm, about 21 mm, about 23 mm, about 25 mm, about 27 mm, about 29 mm, about 31 mm, about 33 mm, and a maximal height of 4 to 18 mm including about 6 mm, about 8 mm, about 10 mm, about 12 mm, about 14 mm or about 16 mm, are intended. These measurements are taken from the natural conditions of the lumbar and cervical spine and assure that the situation with an intervertebral disc prosthesis, as per the invention, comes very close to the in vivo situation.

Further, for an intervertebral disc prosthesis as per the invention one or more X-ray contrast giving markers are provided which are located under the surface of each of the non X-ray contrast giving parts of the prosthesis. That way it is possible to exactly control the position of these parts of the intervertebral disc prosthesis immediately after the implantation. Furthermore, it is possible to check if these parts have changed their position or if they are still in the right position in defined timely intervals.

Further useful measures are described in the dependent claims; the invention is described in the following by examples and figures.

BRIEF DESCRIPTION OF THE DRAWINGS

FIG. 10*a*: stop positioned on the outside of an edge of the middle sliding partner.

DETAILED DESCRIPTION OF VARIOUS AND PREFERRED EMBODIMENTS

Figure 1A:
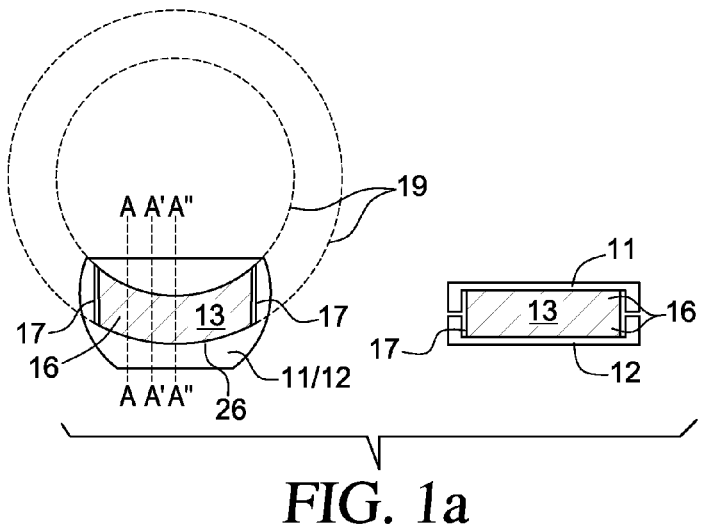
FIG. 1 *a-c* Schematic illustration of a transverse section of a three part intervertebral disc prosthesis, as per the invention, with ventrally curved, articulating convexity and concavity, which are laterally not rounded off (for the lumbar spine)
 a: schematic illustration without edge of the middle sliding partner with median positioning of the convexity and equal position of the upper and lower sliding partner, left median transverse section, right median frontal section
 b: maximally anticlockwise turned upper sliding partner with concavity
 c: maximally clockwise turned upper sliding partner with concavity FIG. 2 *a-c* Schematic depiction of a transverse section of a three part intervertebral disc prosthesis, as per the invention, with ventrally curved, each laterally rounded off articulating convexity and concavity and dorsally displaced articulation area (for the lumbar spine)
 a: schematic depiction without edge of the middle sliding partner with a median positioning of the convexity and equal position of upper and lower sliding partner, left median transverse section, right median frontal section
 b: maximally anticlockwise turned upper sliding partner with concavity
 c: maximally clockwise turned upper sliding partner with concavity FIG. 3 Schematic depiction of sagittal sections in the planes A-A, A'-A', A"-A", of a three part intervertebral disc prosthesis, as per the invention (for the lumbar spine) with
 Top: gap-closure of the sliding partners ventrally
 Middle: gap-closure of the sliding partners dorsally
 Bottom: not inclined sliding partners FIG. 4 *a-c* Schematic depiction of two part intervertebral disc prosthesis, as per the invention, with zero curvation
 a: frontal external view and frontal section
 b: sagittal sections, left without, right with motion in dorsal and ventral direction
 c: transverse section of the upper sliding partner with concavity and dorsally displaced concavity (for the lumbar spine)
Figure 1B:
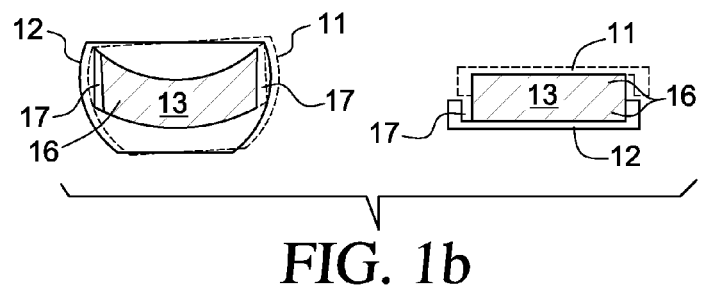
Figure 1C:
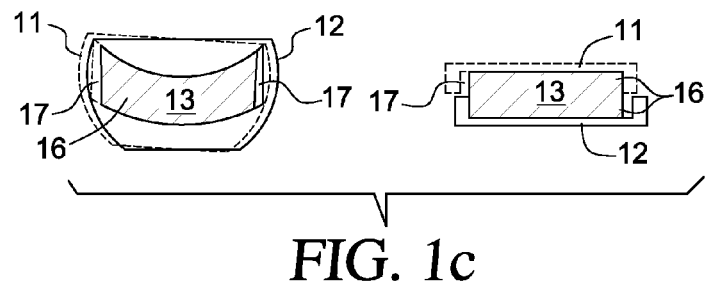

FIGS. 1 *a-c* and 2 *a-c* each show a transversal overview onto the sliding partners 11, 12 of a three part intervertebral disc prosthesis, as per the invention, for the lumbar spine on the left, with curved articulating convexity 16 and concavity 17 and of the middle sliding partner 13 without edge. A limited rotation of upper and lower sliding partner 11, 12, with respect to a fictitious vertical axis of the prosthesis, is made possible due to the curved articulation areas. Convexity 16 and concavity 17 are displaced dorsally in the depicted models.

The ventral and dorsal curvation of the convexity 16 of the middle sliding partner 13 is derived from two circles with different radii but identical mid points. The radii of curvature run in a constant distance towards each other. As per the invention, it is however intended that the secants can laterally run towards each other or diverge. The right part of FIGS. 1 a-c and 2 a-c each schematically show a frontal section of the prosthesis shown on the left. In FIGS. 1 a and 2a the position of the three sections A-A, A'-A', and A"-A" is shown, onto which in FIG. 3, a sagittal view is depicted respectively.

In the left as well as the right parts of FIG. 1 a it can be well seen that in the case of not rotated sliding partners 11, 12, i.e. when the external circumferences of upper and lower sliding partner 11, 12 completely lie above each other in the transversal view, the concavity 17 of the upper and lower sliding partner 11, 12 is shaped a little broader to the left and right of the convexity 16, of the middle sliding partner 13 so that "clearance" for the motion of the convexity 16, of the middle sliding partner 13 within the concavity of the upper sliding partner 11 and the lower sliding partner 12 is given. The convexity 16 is centrally positioned within the concavity 17 in FIG. 1 a.

FIG. 1 b shows the position of the sliding partners 11, 12, 13 of prosthesis, as per the invention, when the upper sliding partner 11, whose position is marked by the dotted line, is rotated fully in anticlockwise direction against the middle sliding partner 13. On the right in FIG. 1 b, it can be seen that the position of the middle sliding partner within the concavity 17 changes thereby as well. The middle sliding partner is shifted up to the right outside of the concavity 17 of the upper sliding partner 11 during the rotation of the upper sliding partner. The rotation is limited by virtue of the contact. FIG. 1 c shows the position of the sliding partners towards each other when the upper sliding partner 11, is rotated maximally in clockwise direction. During this rotation as well, the middle sliding partner moves within the concavity 17 of the lower sliding partner 12. In each of the right part of FIGS. 1 b and c it can be well seen that the external circumferences of upper and lower sliding partner 11, 12 shift during maximal rotation. Upper and lower sliding partners 11, 12 are not in line with respect to their lateral external areas. In the case of an implanted intervertebral disc prosthesis, as per the invention, the rotation of the sliding partners 11, 12 towards each other depicts a rotation, with respect to a fictitious vertical axis, of the prosthesis.

Figure 2A:
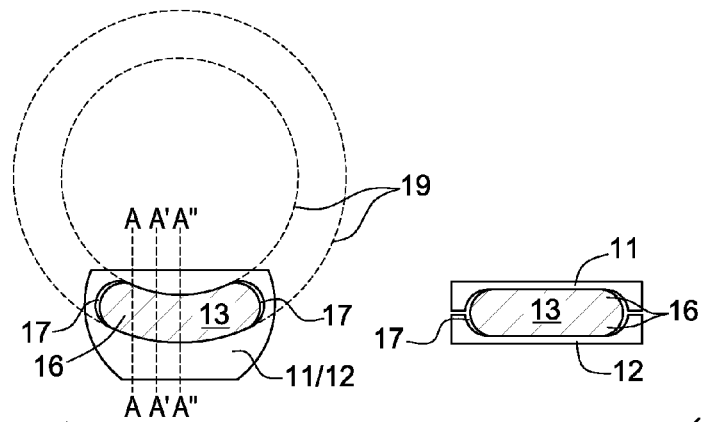
Figure 2B:
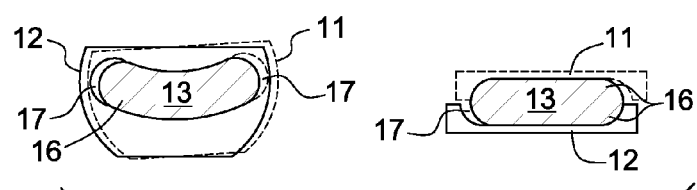
Figure 2C:
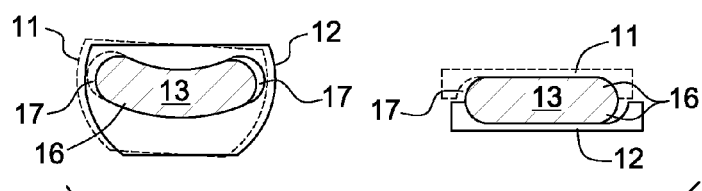

In FIGS. 1 a-c the surfaces of the convexity 16 and concavity 17 each terminate angularly. In FIGS. 2 a-c a design is depicted, as per the invention in which the lateral ends of the convexity 16 and concavity 17 are each rounded off.

Figure 3:
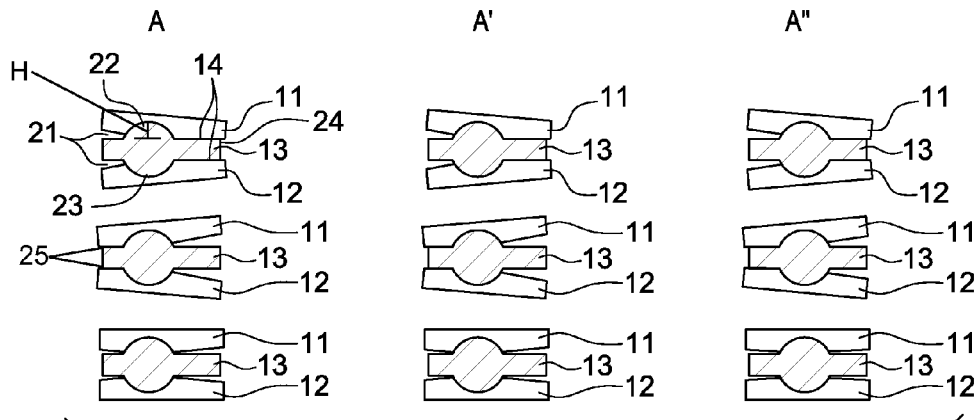

FIG. 3 shows the sagittal sections of the sections A-A, A'-A', A"-A" for the lumbar spine, as depicted in FIGS. 1 a-c and 2 a-c. In each of the above, a ventral gap-closure of the edges 14 of the sliding partners 11, 12, 13 can be seen. By virtue of this the aperture angle 21 of the opposite side of the convex-concave part of the sliding surfaces 22, 23 increases in size. In the middle, a dorsal gap-closure can be seen and in each of the lower parts, sliding partners 11, 12, 13 that are not inclined towards each other. In the three sections it can be well seen how the position of the upper and lower sliding surface 22, 23 are displaced from dorsal to ventral in the direction of the median section, i.e. from section A to A" as a result of the curvation in the transversal plane of the articulation areas.

Figure 4A:
Figure 4B:
Figure 4C:
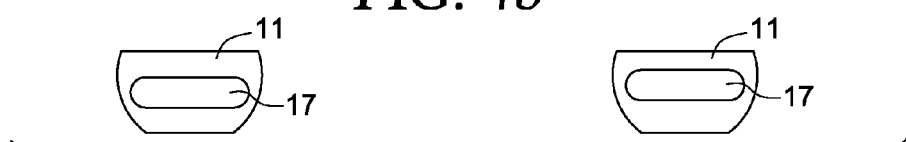

FIG. 4 a-c shows a schematic illustration of a two part intervertebral disc prosthesis, as per the invention, with zero curvation of the convexity in a frontal view (FIG. 4a), sagittal view (FIG. 4b) and transversal view (FIG. 4c).

In FIG. 4a, a frontal external view of a two part intervertebral disc prosthesis, as per the invention, with upper sliding partner 11 and lower sliding partner 12 is depicted on the left. The lower sliding partner 12 may, depending on the design, comprise two parts, as implied by the hatching. Hereby, the part (hatched) providing the convexity 16 is made of a different material than the part (white, non hatched) of the sliding partner 12 directed towards the vertebral body, depending on the design. It is preferred that upper sliding partner 11 and lower sliding partner 12 (white, non hatched part) are made of identical materials and the convexity 16 of a different material. It is also intended that the sliding partners 11, 12 and the convexity 16 are made of the same material.

FIG. 4 a shows on the right a frontal section through a functional two part prosthesis, as per the invention, with upper sliding partner 11, lower sliding partner 12 and convexity 16, with the lower sliding partner comprising two parts.

In FIG. 4 b a sagittal views through a two part intervertebral disc prosthesis, as per the invention can be seen. On the left, the prosthesis can be seen in a position with not inclined sliding partners 11, 12 whereas in 4 b on the right a dorsal and ventral gap-closure is depicted respectively. The convexity 16 is depicted hatched.

FIG. 4 c shows two different overviews onto the inner sides of an upper sliding partner 11 of a two part prosthesis. The concave recess 17, which presents a shape corresponding to a convexity, is delineated. In the right part of the illustration, the concavity is dorsally (lumbar spine) displaced. In the case of a three part intervertebral disc prosthesis FIG. 4 c shows the inner side of the upper and lower sliding partner with the concavity, on the right with a dorsal displacement (lumbar spine).

Figure 5A:
FIG. 5 *a, b* Schematic illustration of a three part intervertebral disc prosthesis, as per the invention with "zero curvation"
 a: frontal external view and frontal section
 b: sagittal sections, left without, right with motion in dorsal and ventral direction FIG. 6 *a-c* Schematic illustration of different shapes of the upper and lower sliding partner for the lumbar spine FIG. 7 *a, b* Schematic illustrations of the arrangement of anchoring teeth on the outsides of the upper and lower sliding partner for the lumbar spine FIG. 8 Schematic depiction of median frontal section of the three part prosthesis with a middle sliding partner without an edge in which the upper and lower sliding partners run non-parallel to one another.
Figure 5B:
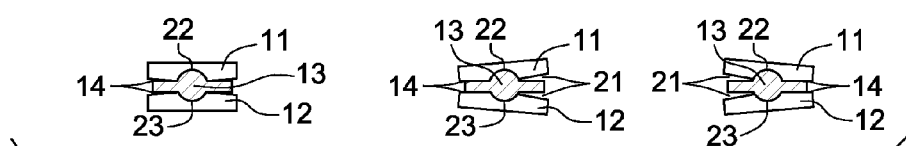

In FIG. 5 a schematic frontal views of a three part intervertebral disc prosthesis, as per the invention, with zero curvation can be seen on the left and right with upper sliding partner 11, lower sliding partner 12 and middle sliding partner 13. FIG. 5 a on the left shows a frontal external view of a functional three part intervertebral disc prosthesis, as per the invention, with cylindrically shaped middle sliding partner 13, which is rounded of at the sides. In FIG. 5 a on the right, a median frontal section of three part intervertebral disc prosthesis, as per the invention, is depicted. It can be well seen in this section, that the height of the middle sliding partner 13 is constant from one side to the other. Because of this, no bending sideways of the sliding partners towards each other is possible with a two part and a three part intervertebral disc prosthesis, as per the invention.

FIG. 5 b shows respective sagittal views of a three part intervertebral disc prosthesis, as per the invention. The upper sliding partner 13, the lower sliding partner 12 as well as the interpositioned middle sliding partner 13 can each be seen. In FIG. 5 b the outer circumferences of the upper and lower convexity are part of a common circle. However, a design is also intended, in which the middle sliding partner 13 is flattened and thus the convexities are not part of a common circular path, but rather peripheral circular segment. Added to that, the radii of upper and lower convexity may differ. The last two stated designs are not depicted in the figures.

In FIG. 5 b on the left, the prosthesis can be seen with no inclined sliding partners 11, 12, 13, whereas in FIG. 5 b on the right a dorsal and ventral gap-closure is depicted respectively. The aperture angle 21 in FIG. 5 b on the right has accordingly increased correspondingly to the closed gap on the opposing side of the concave-convex part of the sliding surfaces 22, 23.

A gap closure between the edges 14 during terminal inclination of the sliding partners 11, 12, 13 arises, so that an optimal load transfer is guaranteed.

Figure 6A:
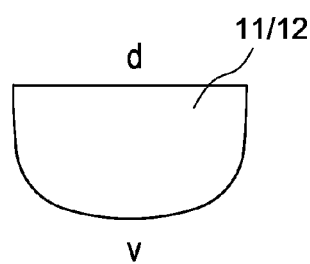
Figure 6B:
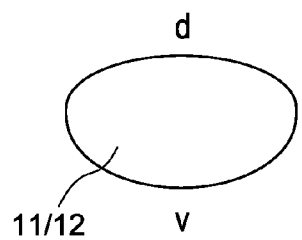
Figure 6C:
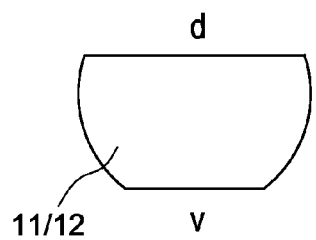

FIGS. 6 a-c each show in an overview onto upper and lower sliding partner 11, 12, schematic alternative designs of the shape of the outer circumference. Hereby the small letters each mark the orientation with respect to the dorsoventral positioning of the plates for the lumbar spine (d=dorsal; v=ventral), which however, are vice versa for the cervical spine (v then dorsal and d then ventral).

Figure 7A:
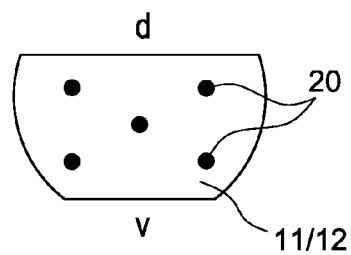
Figure 7B:
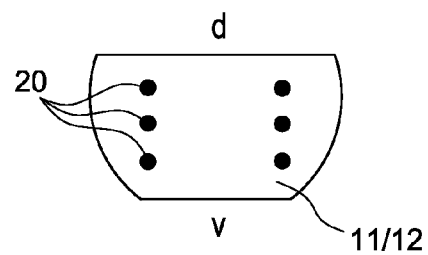
Figure 8:
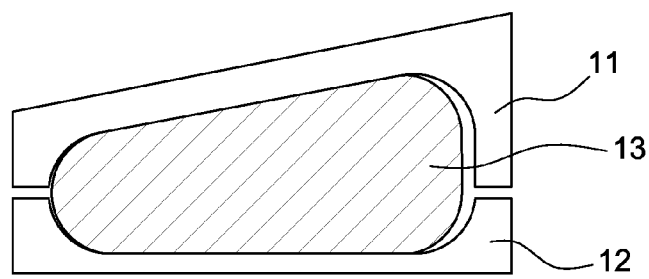
Figure 9:
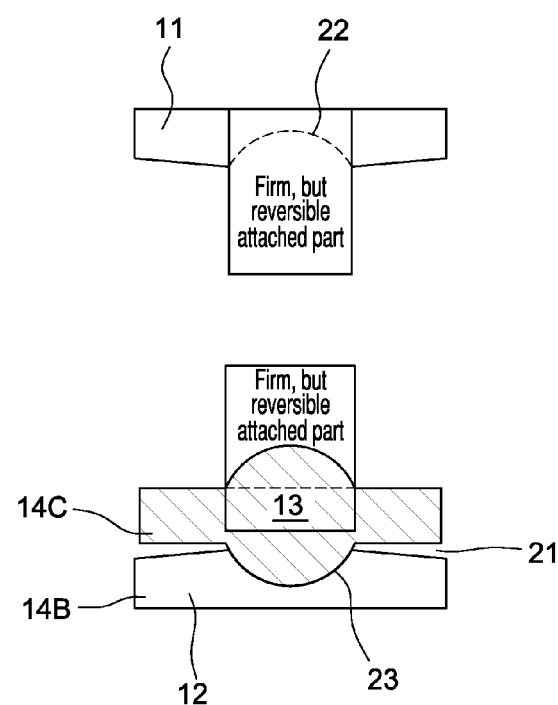
FIG. 9 Schematic representation of a permanent or firm, but reversible assembly.
Figure 10A:
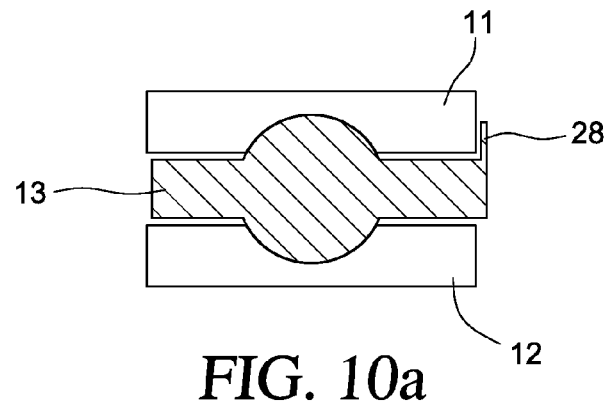
FIGS. 10*a, b* to 12 Schematic representations of a safeguard against slip out
Figure 10B:
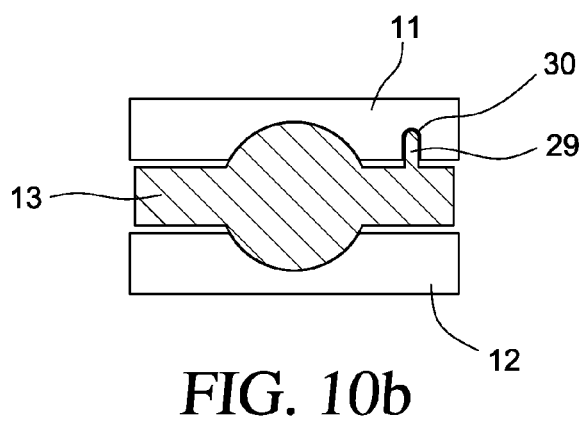
FIG. 10*b*: stop adapted to be guided within a slot of the edge of the middle sliding partner.
Figure 11:
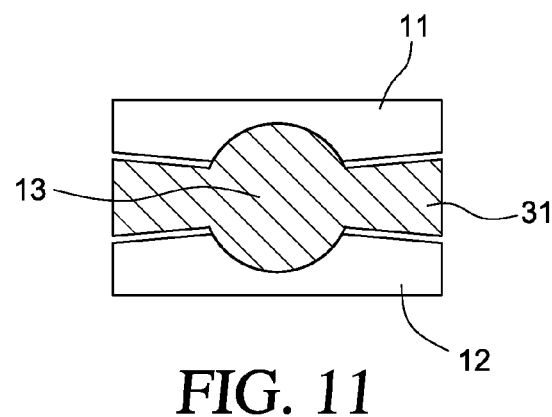
FIG. 11: dovetail shaped edge of middle sliding partner.
Figure 12:
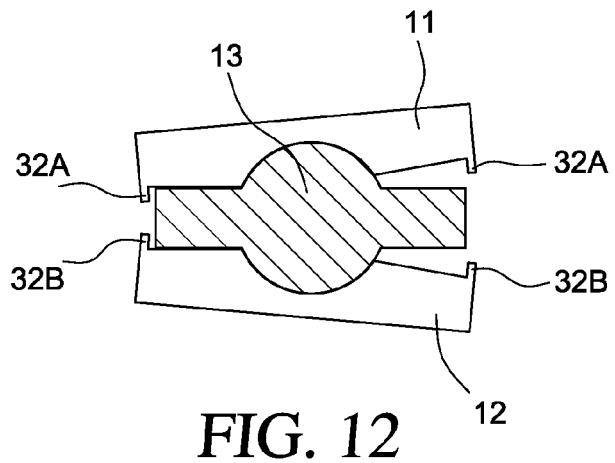
FIG. 12: hooked-shaped peripheral area of the edges of the upper and lower sliding partners.
Figure 13:
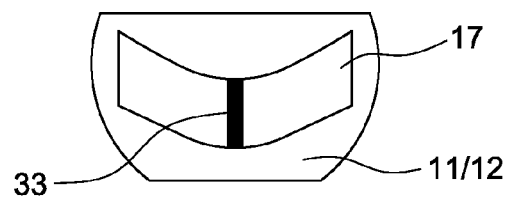
FIG. 13: Schematic representation of a bar in the concavity.
Figure 14:
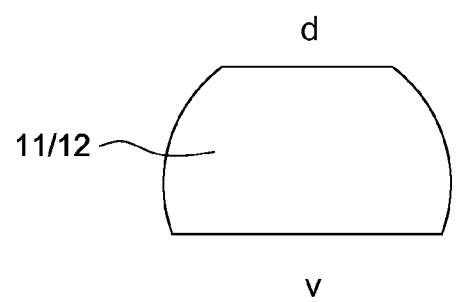
FIG. 14: Schematic illustration of the upper/sliding partner for the lumbar spine having dorsally tapering off radii.
Figure 15:
FIG. 15: Schematic illustration of a convexity with an asymmetrical ventrally arched curvation.
Figure 16:
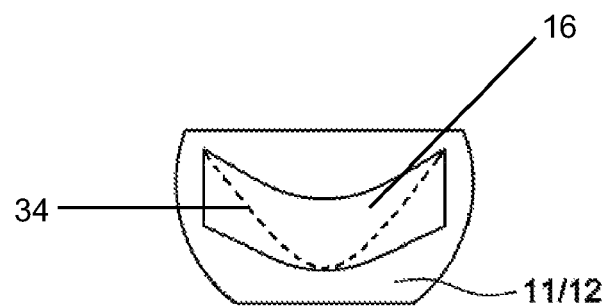
FIG. 16: Schematic depiction of arched curvations of the convexity with the ventral and dorsal radii curved differently.

In FIGS. 7 a and 7 b alternative arrangements for the anchoring teeth 20 on the outside of the upper and lower sliding partner 11, 12 for the lumbar spine are depicted. Again the orientation of the sliding partners with respect to the dorsoventral orientation is indicated by the small letters (d=dorsal; v=ventral). Dorsally in the middle no anchoring teeth 20 are intended, because this results in sparing the vertebral bodies and facilitates the implantation. The arrangement of the anchoring teeth allows for an implantation of the intervertebral disc prosthesis from ventral as well ventrolateral and lateral. For the cervical spine the reversed orientation applies, also without middle dorsal anchoring teeth 20.

The shown designs of a two-part as well as a three-part intervertebral disc prosthesis, as per the invention, in the figures are only exemplary and not definite. Once given the above disclosure, many other features, modifications, and improvements will become apparent to the skilled artisan. Such other features, modifications, and improvements are therefore considered to be part of this invention.

REFERENCE NUMBERS 11 upper sliding partner
12 lower sliding partner
13 middle sliding partner
14 edge
16 convexity
17 concavity
19 circumference
20 anchoring teeth
21 aperture angle
22 upper articulation area
23 lower articulation area
24 outer rim
25 gap closure
26 arched curvation
27 assymertrical curvation
28, 29 stops of the middle sliding partner
30 groove for stop 29
31 dovetail shaped edge
32A/B hooks at periphery of upper/lower sling partner
33 bar
34 dorsally/ventrally differing radii

The invention claimed is:

1. An intervertebral disc prosthesis for total replacement of an intervertebral disc within a lumbar or cervical spine, comprising
an upper sliding partner adapted to firmly assemble to an upper vertebral body and a lower sliding partner adapted to firmly assemble to a lower vertebral body and a middle sliding partner located between the upper and lower sliding partners, wherein said sliding partners articulate with respect to each other and wherein
a) the middle sliding partner has an upper and lower surface where the upper and lower surfaces each have a convexity, and
b) the upper and lower sliding partner each has a concavity corresponding to the convexity of the upper and lower surfaces of the middle sliding partner, respectively, and the convexities of the upper and lower surfaces of the middle sliding partner and the concavities of the upper and lower sliding partners correlate to a cylinder along its longitudinal axis laterally from right to left, wherein the cylinder has a transversal ventrally directed arched curvature and the concavities of the upper and lower sliding partners are surrounded dorsally, ventrally and laterally, at both sides, by edges,
c) wherein the edges extend between an outer rim and each concavity of the upper and lower sliding partners define an outwardly opening aperture angle upon assembly, and wherein
a. no inclination of the upper and lower sliding partners towards each other in the lateral direction is possible, and
b. a maximal possible motion of the sliding partners in dorsoventral direction is limited by a gap-closure of the outwardly opening aperture angle defined by the edges of the upper and lower sliding partners, and
d) wherein rotation of the upper, middle and lower sliding partners towards each other is limited by a tolerance laterally right and left of the convexities and concavities.

2. An intervertebral disc prosthesis according to claim 1, wherein the middle sliding partner further comprises an edge which surrounds each of the convexities, wherein the edges of the upper, middle and lower sliding partner define said outwardly opening aperture angle and said maximal possible motion.

3. An intervertebral disc prosthesis, according to claim 1 or 2, wherein the upper, lower and/or middle sliding partners have a greater inclination towards each other in ventral direction than in dorsal direction.

4. An intervertebral disc prosthesis according to claim 2, wherein the maximal possible motion of the upper, the lower and the middle sliding partners is defined by
a) a radius of the curvature of the convexities and concavities, a height of the convexities and concavities and a height of the edges of the upper, the lower and the middle sliding partners at dorsoventral inclination of the upper, the lower and the middle sliding partners towards each other, and
b) the aperture angle between the edges of the upper, the lower and the middle sliding partners, wherein the edges of the upper, lower and middle sliding partner run at an incline and/or horizontally with reference to the neighboring edges of the upper, lower and middle sliding partners, wherein during terminal contact of the upper, the lower and the middle sliding partners the gap-closure occurs, and
c) the transversally arched curvature of each convexity and the corresponding concavities and its extent and said tolerance laterally right and left of the convexities and concavities at the rotation of the upper, the lower and the middle sliding partners, with respect to a fictitious vertical axis.

5. An intervertebral disc prosthesis according to claim 1 or 2, wherein the upper, middle and lower sliding partners are constructed in one piece.

6. An intervertebral disc prosthesis according to claim 1 or 2, wherein at least one of the convexities is permanently or reversibly attached to the middle sliding partner, and/or at least one of the concavities is permanently or reversibly attached to the upper and/or lower sliding partner or wherein each convexity and/or the concavities have suitable means for a permanent or firm, but reversible assembly with the respective sliding partner on their base.

7. An intervertebral disc prosthesis according to claim 2, wherein the upper, lower and middle sliding partners and each convexity and/or the concavities as well as the surrounding edges of the upper, lower and middle sliding partners comprise the same or different materials.

8. An intervertebral disc prosthesis according to claim 1 or 2, wherein the surfaces of the sliding partners and/or of parts attached to each other are coated either equally or differently.

9. Intervertebral disc prosthesis according to claim 6, wherein a tongue and groove assembly, a track and corresponding recess, a snap mechanism, gluing or screwing provides for permanent or reversible assembly.

10. An intervertebral disc prosthesis according to claim 1 or 2, wherein the upper and lower sliding partners comprise of one material or the upper and lower sliding partner are coated with said one material and the middle sliding partner is made of a different material or is coated with said different material or all sliding partners comprise or are coated with said one material.

11. Intervertebral disc prosthesis according to claim 1 or 2, wherein each convexity has a maximal height and the maximal height of at least one of the convexities which correlates to a cylinder is less than a radius of said cylinder.

12. An intervertebral disc prosthesis according to claim 1 or 2, wherein a radius of curvature of each of the convexities on the upper and lower surface of the middle sliding partner as well as each corresponding concavity of the upper and lower sliding partners are identical or different.

13. An intervertebral disc prosthesis according to claim 1 or 2, wherein the aperture angle is, upon one-sided gap-closure of the sliding partners during extension or flexion, maximal between 6 and 10 degrees with a tolerance of an additional 3 degrees in every direction.

14. An intervertebral disc prosthesis according to claim 1 or 2, wherein the ventrally directed arched curvature of the convexities and concavities, when in use, slows down rotation around a fictitious central vertical axis between the upper and middle sliding partners and/or the middle and lower sliding partners.

15. An intervertebral disc prosthesis according to claim 1 or 2, wherein the convexities and the respective corresponding concavities are dorsally displaced up to 4 mm away from a central sagittal section.

16. An intervertebral disc prosthesis according to claim 1 or 2, wherein each convexity of the middle sliding partner is asymmetrical, perpendicular, otherwise angled, semispherical rounded off or flattened in both outer lateral regions.

17. An intervertebral disc prosthesis according to claim 2, wherein as an additional safeguard for the middle sliding partner against a slip-out out of the prosthesis during gap closure of all three sliding partners, a stop is part of the edge of the middle sliding partner, that is, upon assembly, located outside the upper sliding partner and/or lower sliding partner, and wherein the stop on at least its upper or lower side is higher than the edge of the middle sliding partner.

18. An intervertebral disc prosthesis according to claim 2, wherein as an additional safeguard for the middle sliding partner against a slip-out out of the prosthesis during a gap-closure of all three sliding partners, a stop is part of the edge of the middle sliding partner, which is higher on the upper and/or the lower side than the edge of the middle sliding partner and is guided within a groove in an edge area of the upper and/or lower sliding partner wherein a clearance is provided for maximal sliding motions of the sliding partners.

19. An intervertebral disc prosthesis according to claim 2, wherein as an additional safeguard for a middle sliding partner with edge against a slip-out out of the prosthesis during a gap-closure of all three sliding partners, the edge of the middle sliding partner increases continuously in height from a transition area of each convexity to a periphery and the edges of the upper and/or lower sliding partners level off to the same degree.

20. An intervertebral disc prosthesis according to claim 2, wherein as an additional safeguard for the middle sliding partner with the edge against a slip-out out of the prosthesis during a gap-closure of the three sliding partners, the most outward portion of the edges of the upper sliding partner and/or lower sliding partner are completely or partially hook-shaped, perpendicular, otherwise angular, curved or a combination thereof in a direction of the other one of such upper sliding partner and/or lower sliding partner, respectively.

21. An intervertebral disc prosthesis according to claim 1, wherein a surface and shape of an outer circumference of the upper and lower sliding partner are equal or unequal and can thereby be adapted to a corresponding size of the vertebral body to which they are to be assembled.

22. An intervertebral disc prosthesis according to claim 1, wherein an outside of the upper and/or lower sliding partner, in a frontal and/or sagittal view, run parallel or non parallel to a respective inside of the upper and/or lower sliding partner.

23. An intervertebral disc prosthesis according to claim 1 or 2, wherein the convexities of the upper and lower surfaces of the middle sliding partner are parallel or non parallel with respect to a horizontal and thus run in a defined angle relative to each other, with the convexities being symmetrical or asymmetrical.

24. An intervertebral disc prosthesis according to claim 1 or 2, wherein the transversal ventrally arched curvature of each convexity and corresponding concavity is designed symmetrically or asymmetrically from a center to both lateral sides of the middle sliding partner.

25. An intervertebral disc prosthesis according to claim 24, wherein the convexity has a discontinuation in the middle and the corresponding concavity has a discontinuation in the form of a bar.

26. An intervertebral disc prosthesis according to claim 1, wherein the upper and lower sliding partners are plane or convex and coated bio-actively.

27. An intervertebral disc prosthesis according to claim 1, wherein the upper and/or lower sliding partner is configured to engage an instrument for implantation or explantation.

28. An intervertebral disc prosthesis according to claim 1, wherein the intervertebral disc prosthesis has a maximal breadth in a frontal view of 14 to 48 mm, a maximal depth in a sagittal view of 11 to 35 mm and a maximal height of 4 to 18 mm.

29. An intervertebral disc prosthesis according to claim 1 or 2, wherein the intervertebral disc prosthesis is suitable for implantation into a lumbar spine, wherein an outer circumference of the upper and lower sliding partners tapers off ventrally in a transversal view.

30. An intervertebral disc prosthesis according to claim 1 or 2, wherein the intervertebral disc prosthesis is suitable for implantation into a cervical spine, wherein an outer circumference of the upper and lower sliding partner tapers off dorsally in a transversal view.

31. An intervertebral disc prosthesis according to claim 1 or 2, wherein the intervertebral prosthesis has non X-ray contrast giving parts that are each marked under their surface with one or more radiolucent tags.

32. An intervertebral disc prosthesis according to claim 1, wherein each convexity of the middle sliding partner extends completely across the middle sliding partner's upper and lower side, respectively.

33. An intervertebral disc prosthesis according to claim 1 or 2, wherein the transversal ventrally directed arched curvature of the convexitites and the corresponding concavities have a ventral and a dorsal radius that is equal or different.

34. An intervertebral disc prosthesis according to claim 14, wherein a limited rotation motion between the sliding partners with respect to a fictitious central vertical axis is up to 3 degrees for the lumbar spine, and up to 6 degrees for the cervical spine to every side, with a tolerance of an additional 2 degrees to every side.

35. An intervertebral disc prosthesis according to claim 1, wherein the upper and lower sliding partners are blunt on their outer surfaces and have, for their primary anchorage with vertebral bodies, special anchoring teeth, that are either arranged from dorsal to ventral straight or at an incline or in lateral direction, wherein in a respective dorsal row has only laterally arranged anchoring teeth.

36. An intervertebral disc prosthesis according to claim 1 or 2, wherein the convexities on the upper and lower surfaces of the middle sliding partner, each has, along it's longitudinal axis, a one-sided conically diminishing radius.

37. An intervertebral disc prosthesis according to claim 11, wherein the height of the convexities differs on the upper and lower side.

38. An intervertebral disc prosthesis according to claim 2, wherein the edges of the upper, lower and middle sliding partners and each convexity of the middle sliding partner define, upon assembly, the outwardly opening aperture angle.

39. An intervertebral disc prosthesis according to claim 1, wherein a maximal possible motion of the upper, the lower and the middle sliding partners is defined by
  a) a radius of the curvature of the convexities and concavities, a height of the convexities and concavities and a height of the edges of the upper and the lower sliding partners at dorsoventral inclination of the upper and lower sliding partners towards each other,
  b) the aperture angle between edges of the upper and the lower sliding partners, wherein the edges of the upper and lower sliding partners run at an incline and/or horizontally, wherein during terminal contact of the upper and the lower sliding partners the gap-closure occurs, and
  c) the transversally arched curvature of each convexity and the corresponding concavities and its extent and said tolerance laterally right and left of the convexities and concavities at the rotation of the upper, the lower and the middle sliding partners, with respect to a fictitious vertical axis.

40. An intervertebral disc prosthesis according to claim 1, wherein the upper, lower and middle sliding partners and each convexity and/or the concavities of the upper, lower and middle sliding partners as well as the surrounding edges of the upper and lower sliding partners comprise the same or different materials.

\* \* \* \* \*